United States Patent [19]

O'Lenick, Jr.

[11] Patent Number: 5,741,919

[45] Date of Patent: Apr. 21, 1998

[54] COMPLEX MEADOWFOAM ESTERS

[75] Inventor: Anthony J. O'Lenick, Jr., Lilburn, Ga.

[73] Assignee: Fan Tech Ltd., Chicago, Ill.

[21] Appl. No.: 773,735

[22] Filed: Dec. 26, 1996

Related U.S. Application Data

[63] Continuation-in-part of Ser. No. 516,138, Aug. 17, 1995, Pat. No. 5,646,321.

[51] Int. Cl.⁶ ................................................. C07C 57/00
[52] U.S. Cl. ................................................. 554/224
[58] Field of Search ................................. 554/224

[56] References Cited

U.S. PATENT DOCUMENTS 4,425,458  1/1984  Lindner et al. ........................ 524/314
4,868,236  9/1989  O'Lenick ................................ 524/308

OTHER PUBLICATIONS

Morrision & Boyd, Organic Chemistry, 4th ed., p. 828, 1983.

Primary Examiner—Gary Geist
Assistant Examiner—Deborah D. Carr

[57] ABSTRACT

The present invention deals with the composition of matter and the utilization of certain novel complex esters which are prepared by the reaction of meadowfoam oil, meadowfoam fatty acid or methyl meadowfoamate and multi hydroxy compound like pentaerythritol.

5 Claims, No Drawings

COMPLEX MEADOWFOAM ESTERS

RELATED APPLICATIONS

This application is a continuation in part of application Ser. No. 516,138 filed Aug. 17, 1995, now U.S. Pat. No. 5,646,321.

BACKGROUND OF THE INVENTION

1. Field of the Invention

The present invention deals with novel, highly branched complex esters. The compounds are complex esters of multi hydroxy compounds like pentaerythritol reacted with meadowfoam oil, meadowfoam acid or methyl meadowfoamate. The introduction of the meadowfoam portion of the molecule into the compounds of the present invention results in improved liquidity and outstanding emmoliency properties when applied to skin. As will become clear, we refer to the esters of the present invention as complex esters since the hydroxy compound used in the synthesis contains several hydroxyl groups, placed close to each other, resulting in branching in the ester.

2. Description of the Art Practices

Polyoxyalkylene glycol esters based upon linear, saturated compounds are known in the art. Variation of carbon chain lengths in the fatty source has direct effect upon the emulsification properties. While short chain fatty materials result in compounds which are not good emulsifiers, incorporation of fatty groups having more that 12 carbon atoms result in emulsifiers. They are however solids with relatively high melting points.

The use of higher molecular weight unsaturated fatty acids to prepare esters results in products which suffer from oxidative instability and interfere with the fragrance of many products.

The recent availability of meadowfoam oil, with it's 20 to 22 carbon atoms and the specific location of it's double bonds, and it's reaction to make esters results in the preparation liquid stable esters, having outstanding emulsifying properties and are very acceptable for use in personal care applications.

None of the prior amides possess the critical meadowfoam carboxy moiety. Molecules of the current invention have the meadowfoam alkyl group in the ester.

To the extent that the foregoing patent is relevant to the present invention it is herein specifically incorporated by reference. Throughout the specification and claims, percentages and ratios are by weight, pressures are gauge and temperatures are Celsius unless otherwise noted.

THE INVENTION

This invention relates to the use of a particular meadowfoam oil, meadowfoam fatty acid or meadowfoam methyl ester to prepare complex esters made by the reaction of the meadowfoam with a multi hydroxy compound to make a new series of unexpectedly efficient emmolient esters.

Esters are a class of compounds which find applications in many diverse segments of the chemical industry. One of the problems which is encountered using linear fatty acids to make complex esters is the fact that these materials are waxy solids with relatively high melting points. They lack a smooth oily feel on the skin, which is desirable in many cosmetic products.

There are many applications in which liquid esters are desired. One of the ways in which a liquid ester can be made is to incorporate unsaturated groups into the molecule. Selecting unsaturated acids, like oleic acid, however results in an ester which undergoes a degradation process referred to as "rancidity". This makes them unacceptable for applications where odor and taste is an issue. The recent availability of meadowfoam oil, with it's 20 to 22 carbon atoms and the specific location of it's double bonds, and it's reaction with fatty alcohols results in liquid stable ester, acceptable for use in pigmented personal care applications, like make-up and lipstick.

None of the prior compounds possess the critical meadowfoam carboxy moiety. Molecules of the current invention have the meadowfoam alkyl group in the acid portion of the molecule.

THE INVENTION

This invention relates to a particular group of meadowfoam esters based upon meadowfoam oil, meadowfoam methyl ester or meadowfoam fatty acid. The terms meadowfoam oil, fatty acid or methyl ester as used herein refer to a specific alkyl distribution of the groups which is are native to a plant limnathes Alba, commonly called meadowfoam oil. Meadowfoam oil is harvested from a plant and sold commercially by The Fanning Corporation under the tradename "Fancor Meadowfoam".

The unique structure of the oil allows for the synthesis of esters which are liquid and exhibit a high degree of oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of an ester derived the unique distribution of the meadowfoam on the other result in superior liquidity, lubricity, and outstanding oxidative stability.

The compounds of the current invention are specific branched esters conforming to the following structure;

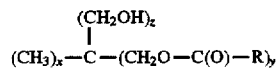

wherein:

R is:
    60–65% by weight
    —$(CH_2)_3$—CH=CH—$(CH_2)_{13}$-$CH3$
    12–20% by weight a mixture of
    —$(CH_2)_3$—CH=CH—$(CH_2)_{15}$—$CH_3$ and
    —$(CH_2)_{11}$—CH=CH—$(CH_2)_7$—$CH_3$ and
    15–28% by weight
    —$(CH_2)_3$—CH=CH—$(CH_2)_6$—CH=CH—$(CH_2)_6$—$CH_3$;

x is and integer ranging from 0 to 1;

z is an integer ranging from 0 to 3;

y is and integer ranging from 1 to 4, with the proviso that x+y+z=4;

PREFERRED EMBODIMENT

In a preferred embodiment x is 0, y is 4 and z is 0.

In a preferred embodiment x is 1, y is 3 and z is 0.

In a preferred embodiment x is 0, y is 3 and z is 1.

In a preferred embodiment x is 1, y is 2 and z is 1.

EXAMPLES

Raw Materials

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

| Example | Description |
|---------|-------------|
| 1 | Meadowfoam Oil |
| 2 | Meadowfoam Fatty Acid |
| 3 | Meadowfoam Methyl Ester |

Hydroxy Compound

EXAMPLE 4

Pentaerythritol

Pentaerythritol is a commercially available tetra functional hydroxy compound conforming to the following structure:

EXAMPLE 5

Another commercially available tri-functional hydroxy compound useful in the synthesis of compounds of the present invention conforms to the following structure:

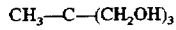

Ester Synthesis

The esterification reaction is carried out using an excess of hydroxy compound or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The ester is prepared by the esterification reaction as shown below:

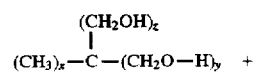

-continued

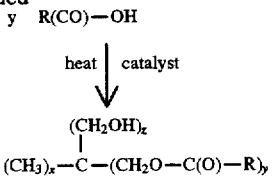

wherein;

x is and integer ranging from 0 to 1;

z is an integer ranging from 0 to 3;

y is and integer ranging from 1 to 4, with the proviso that x+y+z=4;

R is derived from meadowfoam oil.

It should be clear that the value of z is determined by the amount of meadowfoam used relative to hydroxyl compound. If a 1:1 mole ratio (hydroxyl:acid) is used z will be 0. If a mole ratio of 1:0.3 (hydroxyl:acid) is used z will be 3.

GENERAL PROCEDURE

To the specified number of grams of meadowfoam (Examples 1–3) is added the specified number of grams of the specified hydroxyl compound (Example 4–5). Next add 0.1% stannous oxylate based upon the total weight of the batch after all ingredients have been charged, under agitation. The temperature of the mass is raised to 180°–200° C. and water is stripped off as formed. The acid value and hydroxyl value drop to vanishingly small values, and the saponification value increases to theoretical. The products are clear liquids and are liquid to extraordinary temperatures. They exhibit outstanding lubrication properties and are outstanding viscosity index modifiers.

EXAMPLE 6

To 354.0 grams of meadowfoam oil (examples 1) is added the 34.0 grams of the specified hydroxy compound (example 4). Next add 0.1% stannous oxylate based upon the total weight of the batch after all ingredients have been charged, under agitation. The temperature of the mass is raised to 180°–200° C. and water is stripped off as formed. The acid value and hydroxyl value drop to vanishingly small values, and the saponification value increases to theoretical.

Example 6 is repeated only this time the type and quantity of hydroxy compound and meadowfoam derivative are substituted for the meadowfoam oil specified in Example 11.

Class 1 x and z are 0; y is 4

| | Hydroxy Compound | | Meadowfoam Type | |
|---------|---------|-------|---------|-------|
| Example | Example | Grams | Example | Grams |
| 7 | 4 | 34.0 | 1 | 354.0 |
| 8 | 4 | 34.0 | 2 | 354.0 |
| 9 | 4 | 34.0 | 3 | 354.0 |
| 10 | 4 | 34.0 | 1 | 354.0 |
| 11 | 4 | 34.0 | 2 | 354.0 |
| 12 | 4 | 34.0 | 3 | 354.0 |
| 13 | 4 | 34.0 | 1 | 354.0 |
| 14 | 4 | 34.0 | 2 | 354.0 |

Class 2 x is 1 z is 0 y is 3

| Example | Hydroxy Compound Example | Grams | Meadowfoam Type Example | Grams |
|---|---|---|---|---|
| 15 | 5 | 39.0 | 1 | 354.0 |
| 16 | 5 | 39.0 | 2 | 354.0 |
| 17 | 5 | 39.0 | 3 | 354.0 |
| 18 | 5 | 39.0 | 1 | 354.0 |
| 19 | 5 | 39.0 | 2 | 354.0 |
| 20 | 5 | 39.0 | 3 | 354.0 |
| 21 | 5 | 39.0 | 1 | 354.0 |
| 22 | 5 | 39.0 | 2 | 354.0 |

Class 3 x is 0 z is 1 y is 3

| Example | Hydroxy Compound Example | Grams | Meadowfoam Type Example | Grams |
|---|---|---|---|---|
| 23 | 4 | 25.0 | 3 | 354.0 |
| 24 | 4 | 25.0 | 1 | 354.0 |
| 25 | 4 | 25.0 | 2 | 354.0 |
| 26 | 4 | 25.0 | 3 | 354.0 |
| 27 | 4 | 25.0 | 1 | 354.0 |
| 28 | 4 | 25.0 | 2 | 354.0 |
| 29 | 4 | 25.0 | 3 | 354.0 |
| 30 | 4 | 25.0 | 1 | 354.0 |

Class 4 x is 1 z is 1 y is 2

| Example | Hydroxy Compound Example | Grams | Meadowfoam Type Example | Grams |
|---|---|---|---|---|
| 31 | 5 | 30.0 | 1 | 354.0 |
| 32 | 5 | 30.0 | 2 | 354.0 |
| 33 | 5 | 30.0 | 3 | 354.0 |
| 34 | 5 | 30.0 | 4 | 354.0 |
| 35 | 5 | 30.0 | 5 | 354.0 |
| 36 | 5 | 30.0 | 6 | 354.0 |
| 37 | 5 | 30.0 | 7 | 354.0 |
| 38 | 5 | 30.0 | 8 | 354.0 |

The compounds of the invention are liquid esters that have an exceptionally dry feel on the skin.

I claim:

1. A compound which conforms to the following structure:

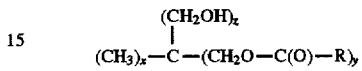

wherein:

R is:
   60–65% by weight —$(CH_2)_3$—CH=CH—$(CH_2)_{13}$—$CH_3$

12–20% by weight a mixture of
   —$(CH_2)_3$—CH=CH—$(CH_2)_{15}$—$CH_3$ and
   —$(CH_2)_{11}$—CH=CH—$(CH_2)_7$—$CH_3$ and 15–28% by weight
   —$(CH_2)_3$—CH=CH—$(CH_2)_6$—CH=CH—$(CH_2)_6$—$CH_3$;

x is and integer ranging from 0 to 1;

z is an integer ranging from 0 to 3;

y is and integer ranging from 1 to 4, with the proviso that x+y+z=4.

2. A compound of claim 1 wherein x is 0, z is 0, and y is 4.

3. A compound of claim 1 wherein x is 1, z is 0, and y is 3.

4. A compound of claim 1 wherein x is 0, z is 1, and y is 3.

5. A compound of claim 1 wherein x is 1, z is 1, and y is 2.

* * * * *